United States Patent [19]

Chang et al.

[11] Patent Number: 5,266,478

[45] Date of Patent: Nov. 30, 1993

[54] ANTIBODIES WHICH TARGET A NEUTRALIZATION SITE WITHIN THE SECOND VARIABLE REGION OF HUMAN IMMUNODEFICIENCY VIRUS TYPE 1 GP120

[75] Inventors: Tse W. Chang; Michael S. C. Fung, both of Houston; Bill N. C. Sun; Cecily R. Y. Sun, both of Bellaire, all of Tex.

[73] Assignee: Tanox Biosystems, Inc., Houston, Tex.

[21] Appl. No.: 797,692

[22] Filed: Nov. 25, 1991

Related U.S. Application Data

[63] Continuation-in-part of Ser. No. 767,533, Sep. 26, 1991, which is a continuation of Ser. No. 137,861, Dec. 24, 1987, abandoned, which is a continuation-in-part of Ser. No. 57,445, May 29, 1987, abandoned, and a continuation-in-part of Ser. No. 692,299, Apr. 26, 1991.

[51] Int. Cl.$^5$ ............... C07K 15/28; C07K 15/00; C12P 21/08; C12N 5/12
[52] U.S. Cl. ............... 435/240.27; 530/387.3; 530/388.35; 530/387.9; 530/387.1; 530/391.3; 530/327
[58] Field of Search ............ 530/387.1, 387.3, 388.35, 530/327, 391.3, 387.9; 435/240.27

[56] References Cited

PUBLICATIONS

Waldmann et al. Science vol. 252 p. 1657, 1991.
Reichmann et al. Nature vol. 332 1988 p. 323.
Lambert Journal of Biological Chemistry vol. 260 No. 22, 12035, 1985.
Gosting et al. Journal of Clinical Micro-vol. 25 No. 5, 845 1987.
Kent et al. abstract 1991.
Stephans et al. abstract 1991.
Fung et al. abstract 1991.
Silvera et al. abstract 1991.

*Primary Examiner*—David L. Lacey
*Assistant Examiner*—Lila Feisee
*Attorney, Agent, or Firm*—Eric P. Mirabel

[57] ABSTRACT

Disclosed are monoclonal antibodies and related products which bind to the second variable region of HIV-1 gp120 and synthetic peptides and anti-idiotypic antibodies which induce endogenous production of antibodies with these same properties.

4 Claims, 1 Drawing Sheet

Figure 1

| | Monoclonal antibodies | | |
|---|---|---|---|
| | BAT085 (γ1,k) | G3-136 (γ1,k) | G3-4 (γ2a,k) |
| Neutralization<br>  HIV-1 IIIB<br>  HIV-1 MN<br>  HIV-1 RF | +<br>-<br>- | +<br>-<br>++ | +<br>-<br>++ |
| Infected cell staining<br>  HIV-1 IIIB<br>  HIV-1-MN<br>  HIV-1 RF | ++<br>+<br>- | +<br>-<br>++ | +<br>-<br>++ |
| sCD4 inhibition of gp120 binding | - | + | + |
| Deglycosylation of gp120 on binding | No effect | Reduced | Abolished |
| Disulfide bond reduction of gp120 on binding | No effect | Reduced | Abolished |
| Binding to epitope peptide (a.a.#:169-183) | ++ | + | - |

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:1:

Val Gln Lys Glu Tyr Ala Phe Phe Tyr Lys Leu Asp Ile Ile Pro
1               5                   10                  15

( 2 ) INFORMATION FOR SEQ ID NO:2:

( i ) SEQUENCE CHARACTERISTICS:
    ( A ) LENGTH: 20 amino acids
    ( B ) TYPE: amino acid
    ( D ) TOPOLOGY: linear ( x i ) SEQUENCE DESCRIPTION: SEQ ID NO:2:

Leu Asp Ile Ile Pro Ile Asp Asn Asp Thr Thr Ser Tyr Ser Leu Thr Ser
1               5                   10                  15
Cys Asn Thr
        20

( 2 ) INFORMATION FOR SEQ ID NO:3:

( i ) SEQUENCE CHARACTERISTICS:
    ( A ) LENGTH: 15 amino acids
    ( B ) TYPE: amino acid
    ( D ) TOPOLOGY: linear ( x i ) SEQUENCE DESCRIPTION: SEQ ID NO:3:

Phe Asn Ile Ser Thr Ser Ile Arg Gly Lys Val Gln Lys Glu Tyr
1               5                   10                  15

( 2 ) INFORMATION FOR SEQ ID NO:4:

( i ) SEQUENCE CHARACTERISTICS:
    ( A ) LENGTH: 10 amino acids
    ( B ) TYPE: amino acid
    ( D ) TOPOLOGY: linear ( x i ) SEQUENCE DESCRIPTION: SEQ ID NO:4:

Val Gln Lys Glu Tyr Ala Phe Phe Tyr Lys
1               5                   10

( 2 ) INFORMATION FOR SEQ ID NO:5:

( i ) SEQUENCE CHARACTERISTICS:
    ( A ) LENGTH: 10 amino acids
    ( B ) TYPE: amino acid
    ( D ) TOPOLOGY: linear ( x i ) SEQUENCE DESCRIPTION: SEQ ID NO:5:

Ala Phe Phe Tyr Lys Leu Asp Ile Ile Pro
1               5                   10

( 2 ) INFORMATION FOR SEQ ID NO:6:

(i) SEQUENCE CHARACTERISTICS:
    (A) LENGTH: 15 amino acids
    (B) TYPE: amino acid
    (D) TOPOLOGY: linear (xi) SEQUENCE DESCRIPTION: SEQ ID NO:6:

| Met | Gln | Lys | Glu | Tyr | Ala | Leu | Leu | Tyr | Lys | Leu | Asp | Ile | Val | Ser |
|---|---|---|---|---|---|---|---|---|---|---|---|---|---|---|
| 1 | | | | 5 | | | | | 10 | | | | | 15 |

(2) INFORMATION FOR SEQ ID NO:7:

(i) SEQUENCE CHARACTERISTICS:
    (A) LENGTH: 15 amino acids
    (B) TYPE: amino acid
    (D) TOPOLOGY: linear (xi) SEQUENCE DESCRIPTION: SEQ ID NO:7:

| Thr | Gln | Lys | Lys | Tyr | Ala | Leu | Phe | Tyr | Lys | Leu | Asp | Val | Val | Pro |
|---|---|---|---|---|---|---|---|---|---|---|---|---|---|---|
| 1 | | | | 5 | | | | | 10 | | | | | 15 |

ANTIBODIES WHICH TARGET A NEUTRALIZATION SITE WITHIN THE SECOND VARIABLE REGION OF HUMAN IMMUNODEFICIENCY VIRUS TYPE 1 GP120

RELATED APPLICATIONS

The application is a continuation-in-part of Ser. No. 07/767,533, filed Sep. 26, 1991, which is a continuation of Ser. No. 07/137,861, filed Dec. 24, 1987 (now abandoned), which is a continuation-in-part of Ser. No. 07/057,445, filed May 29, 1987, (now abandoned) and this application is also a continuation-in-part of Ser. No. 07/692,299, filed Apr. 26, 1991. Priority is hereby claimed to all these applications.

BACKGROUND OF THE INVENTION

It has become evident that humoral responses play crucial roles in the protective immunity against infection by HIV-1, and in preventing its progression to disease states. It has been demonstrated that higher endogenous neutralizing antibody titers correlate with better clinical conditions, and low or decreasing neutralizing antibody titers with disease progression. Wendler I., V. Bienzle, and G. Hunsman, *AIDS Res. Human Retroviruses* 3:157–163 (1987). It has also been demonstrated that ARC and AIDS patients treated with hyperimmune plasma from asymptomatic HIV-1 seropositive individuals showed clinical improvement, which correlated with reduction in HIV-1 viraemia. Jackson C. G., et al., *Lancet* 2:647–651 (1988); Karpas A., et al., *Proc. Natl. Acad. Sci. USA* 87:7613–7617 (1990); Karpas A., et al., *Proc. Natl. Acad. Sci. USA* 85:9234–9237 (1988). More recently, some preliminary studies showed that chimpanzees injected with a mouse-human chimeric HIV-1 neutralizing monoclonal antibody (MAb) were protected from infection by the virus. Emini E. A. et al. vol. 2, p. 72. Th. A. 64. Abstr. *VII International Conference on AIDS* (1991). In short, monoclonal antibodies which neutralize HIV-1 infection are likely to be useful in post-exposure prophylaxis and in therapy.

The envelope proteins of HIV-1, gp120 and gp41, are known to be the major targets for the HIV-1 neutralizing activity in the sera of HIV-1-infected individuals, and of animals immunized with the viral proteins. Several neutralization sites have been identified in gp120, including an immunodominant epitope in the V3 region (amino acid residues: 308–322), commonly known as the principal neutralization determinant (PND). See International Application No. PCT/US88/01797. Antibodies raised against this continuous epitope usually exhibit neutralizing activity.

Anti-PND antibodies do not block virus binding to CD4 on T cells, but prevent virus internalization by the T cells subsequent to CD4 binding. Skinner M. A., et al. *J. Virol.* 62:4195–4200 (1988). Another continuous neutralization site on gp120 is located in the CD4 region (amino acid residues: 413–447), which is involved in CD4-gp120 interaction. International Patent Application No. PCT/US90/02261. Antibodies to this region exhibit broad neutralizing activity against divergent HIV-1 isolates, but this neutralization site appears to be rather immunosilent in HIV-1 infected individuals. Sun N. C., et al., *J. Virol.* 63:3579–3585 (1989).

Sera from most HIV-1 infected individuals usually have low levels of broadly HIV-1 neutralizing antibodies, and such neutralizing antibodies as are present are usually directed to conformational or discontinuous epitopes on gp120. For example, a human MAb, designated I5e, which recognizes a discontinuous epitope on gp120, has been shown to be involved in CD4 binding and in antibody neutralization of multiple HIV-1 isolates. Ho D. D., et al., *J. Virol*, 65:489–493 (1991). Another HIV-1 neutralizing murine MAb, designated G3-4, which identified another distinct conformational epitope on gp120, is involved in the interaction with CD4. U.S. application Ser. No. 07/692,099 (pending).

Some other MAbs which neutralize HIV-1 are described below.

SUMMARY OF THE INVENTION

The invention includes MAbs which define a unique neutralization domain in the V2 region of HIV-1 gp120, and related and derivative products, such as synthetic peptides and anti-idiotypic antibodies which can induce production of antibodies with such characteristics. Two of the antibodies of the invention are designated BAT085 and G3-136, and both of them are IgG$_{1,k}$ and bind to the peptidic segment V15P (amino acid residues: 169-183) in HIV-1 IIIB gp120.

The uses for the antibodies of the invention include therapy for HIV-1 or AIDS, post-exposure prophylaxis, and diagnosis of HIV-1 infection. The synthetic peptides and anti-idiotypic antibodies of the invention can be used in active immunization to induce endogenous production of neutralizing antibodies of the invention. The synthetic peptides and anti-idiotypic antibodies of the invention can also be used as diagnostic reagents to detect the presence or concentration of neutralizing antibodies, or concentration of the MAbs of the invention, in a serum sample.

BRIEF DESCRIPTION OF THE DRAWINGS

FIG. 1 summarizes some of the properties of the MAbs of the invention.

DETAILED DESCRIPTION OF THE INVENTION AND OF MAKING AND USING IT

The MAbs of the invention bind to the HIV-1 viral envelope glycoprotein gp120. In the processing of HIV-1 specific envelope protein in infected T cells, gp41 is a transmembrane protein and is largely not exposed. In contrast, gp120 is an external envelope protein which is extracellular. Thus, in infected T cells the gp120 protein offers binding epitopes for the MAbs of the invention.

More specifically, the MAbs of the invention include MAbs which bind to a neutralizing epitope defined by a peptidic segment (amino acid residues 169-183) in HIV-1 IIIB gp120. Importantly, two of the MAbs of the invention can neutralize different isolates of HIV-1 (i.e., they are broadly reactive).

One of the MAbs of the invention (BAT085) is discussed in abandoned U.S. patent application Ser. No. 07/057,445, and in abandoned application Ser. No. 07/137,861. The hybridoma which produces the MAb G3-136 was deposited on Nov. 20, 1991, at the American Type Culture Collection, 12301 Parklawn Drive Rockville, Md., 20853 under Accession No. HB10932.

Suitable MAbs of the invention are produced by first immunizing an animal, preferably a mouse, with a suitable antigen, which in the case of G3-136 was gp120 purified from the lysates of H9 cells infected with HIV-1 IIIB. The antigen can, however, be in whole form, e.g., whole HIV-1 virions, which were used as the immunogen in producing BAT085. Alternatively, cells infected with a virus and expressing the virus or its antigenic domains can also be used.

The antigenic domains of HIV-1 on gp120, or synthetic or recombinant peptides which have the same or an immunologically equivalent sequence to these antigenic domains can also be used. These synthetic or recombinant peptides for use in immunization can be synthesized by conventional techniques, such as with the RaMPS system (DuPont DeNemours & Co.), which applies Fmoc chemistry. Alternatively, recombinant peptides containing these peptides may be biosynthesized by expressing in *E. coli*, yeast or eukaryotic cells the gene segments containing the appropriate coding sequences, or by using other expression systems.

When using a synthetic peptide segment or a short recombinant peptide as an immunogen, it is usually more effective to conjugate it to a protein carrier, for example, HBsAg, hepatitis B virus core antigen, ovalbumin, bovine serum albumin, or preferably keyhole limpet hemocyanin ("KLH"). If the peptidic segment lacks a lysine residue or if the lysine residue is in the middle part of the segment, it is desirable to add a lysine residue at the C-terminal end. Because the N-terminus already has an α-amino group, the modified synthetic peptide will have two available amino groups for linking.

Multiple molecules of peptides can be conjugated to each molecule of the carrier to make the immunogen. With KLH, a preferred molar ratio for peptide/KLH is 10. The conjugation can be done with well established methods using glutaraldehyde or bis (sulfosuccinimidyl) suberate or preferably disulfosuccinimidyl tartrate as the cross-linkers.

One immunization protocol for preparing the MAbs is to inject into each mouse 50 μg of the conjugate of KLH and the aforementioned recombinant or synthetic peptides in Freund's complete adjuvant. Two and four weeks later, the same amount of antigen is given subcutaneously in Freund's incomplete adjuvant. After about six weeks, the fourth antigen injection is given intraperitoneally in saline. Mice are sacrificed 4 days after the last injection and the spleens (or sometimes the lymph nodes) are removed for preparing single cell suspensions for fusion with myeloma cells.

Lymphocytes from the spleens (or lymph nodes) which have been removed from the mice can be fused with myeloma cells to prepare hybridomas secreting the MAbs of the invention. The fusion procedure with polyethylene glycol and other various procedures concerning the cloning and the culturing of hybridomas have been well established. One preferred protocol is the well-known one described by Hudson, L. and Hay, F. C. (Practical Immunology, 2nd edition, pp. 303-313, 1980, Blackwell Publishing Co., Boston), in which the lymphocytes are fused with non-secreting mouse myeloma cells, such as NS-1 or Sp2/0 cells, using polyethylene glycol. The fusion reagent used to make G3-4 was polyethylene glycol mixed with dimethyl sulfoxide (DMSO) in calcium magnesium-free phosphate buffered saline (PBS).

Reagents other than those discussed can be used for the chemical fusion. Another alternative is to use electrical fusion rather than chemical fusion to form hybridomas. This technique is well-established. Instead of fusion one can also transform a B-cell to make it immortal using, for example, an Epstein Barr Virus or a tranforming gene. (For a method of transforming a B-cell, see "Continuously Proliferating Human Cell Lines Synthesizing Antibody of Predetermined Specificity, "Zurawski, V. R. et al, in *Monoclonal Antibodies*, ed. by Kennett R. H. et al, Plenum Press, N.Y. 1980, pp 19-33.)

The screening of hybridomas for MAbs reactive with the immunogen can be performed with an enzyme linked immunosorbent assay (ELISA). The purified native gp120 is the preferred solid-phase antigen. This preparation of gp120 is glycosylated and non-reduced in order to retain the disulfide bridges. The specific procedure used in generating the MAbs of the invention is described below in the following section.

Generally, the MAbs which are first obtained will be murine-derived, and thus may be immunogenic or allergic in human therapy. It is therefore desirable to produce chimeric antibodies (having an animal variable region and a human constant region), or to use human expression vectors (Stratagene Corp., La Jolla, Calif.) to produce fragments of human antibodies ($V_H$, $V_L$, $F_V$, Fd, Fab, or F(ab')$_2$) and then construct whole human antibodies using techniques similar to those for producing chimeric antibodies. In addition, one can create antibodies in which the entire constant portion and most of the variable region is human-derived, and only the antigen binding site is derived from some other mammals. See Riechmann, L. et al., Nature 332:323-327 (1988). Further, one can create single-chain antibodies in which the heavy and light chain $F_v$ regions are connected. See Huston, J. S. et al., Proc. Natl. Acad. Sci. USA 85:5879-5883 (1983).

All of the aforementioned human and humanized antibodies are less immunogenic than other mammalian equivalents, and the fragments and single-chain antibodies are less immunogenic than whole antibodies. All these types of antibodies are therefore less likely to evoke an immune or allergic response. It is noted that an immune response could deplete the antibodies which are administered before such antibodies could function to neutralize virus.

MAbs of the invention can be used to reduce or eliminate the virus infected T cells by antibody-dependent cellular cytotoxicity (ADCC), complement-mediated cytolysis, or other cytolytic or regulatory immune mechanisms. For example, antibodies of certain IgG subclasses, such as mouse IgG$_{2a}$ and human IgG$_1$ and IgG$_3$, can mediate ADCC carried out by certain Fc receptor-bearing phagocytic leukocytes. Administration of such mouse IgG$_{2a}$ antibodies, chimeric antibodies bearing human γ-1 or γ-3 chains, or human IgG$_1$ or IgG$_3$ antibodies can be used to down-regulate or lyse infected T cells.

The MAbs of the invention can also be used for targeting cytotocic agents to HIV-1-infected cells. The MAbs of the invention can also be used as carrier agents of cytotoxic drugs or for delivering an effector substance, by conjugating the MAbs to these substances. A toxin-antibody conjugate will bind and directly kill infected T cells. These toxins are cytolytic or cytotoxic agents, including cytotoxic steriods, gelonin, abrin, ricin, Pseudomonas toxin, diphtheria toxin, pokeweed antiviral protein, tricathecums, radioactive nuclides, and membranelytic enzymes (such as phospholipase).

The antibody and the agent can be conjugated by chemical or by genetic engineering techniques. The toxin-antibody conjugates may be used alone or in combination with the free antibodies of the invention.

The antibodies of the invention (and the toxin conjugates, fragments, and other derivatives) are administered systemically, and preferably intravenously. They can be administered in any pharmaceutically acceptable vehicle.

Another therapeutic alternative involves active immunization, wherein antibodies specific to the epitope bound by the MAbs of the invention are endogenously produced in vivo. These endogenously produced antibodies bind to this epitope and cause destruction of the infected T cells. Production of such antibodies can be induced either by administering an immunogenic peptide, e.g., a recombinant peptide, containing the same sequence (or an immunologically equivalent sequence) as the epitope bound by the mAb of the invention.

Production of such antibodies can also be induced by administering a paratope-specific anti-idiotypic antibody. Anti-idiotype antibodies against the paratope of the antibodies of the invention bear the internal image of the gp120 epitope. These anti-idiotypic antibodies can be used for active immunization to induce the endogenous formation of antibodies against these epitopes.

Such paratope-specific anti-idiotypic antibodies are administered to a patient in an immunogenic amount sufficient to induce the formation of antibodies against infected T cells. These anti-idiotypic antibodies are preferably administered as human or humanized antibodies, or single-chain antibodies, to minimize any immune response against them. They may also be any of the antibody fragments, $V_H$, $V_L$, $F_v$, Fd, Fab, or $F(ab')_2$.

Certain factors, such as granulocyte monocyte-colony stimulating factor (GM-CSF) or monocyte-colony stimulating factor (M-CSF), are known to induce the proliferation of leukocytes, including those mediating ADCC. In in vitro experiments, GM-CSF and M-CSF have been shown to augment the ADCC activity on tumor cells mediated by MAbs specific for surface antigens expressed on the tumor cells. The therapeutic effect of specific MAbs of the invention, conjugates, or polyclonal antibodies in depleting infected T cells could perhaps be enhanced by combining them with factors that augment ADCC activities.

Derivative antibodies can be made which draw cytotoxic cells such as macrophages or cytotoxic T cells toward the targeted T cells. These derivative antibodies include bi-specific antibodies having a specificity for a receptor of a cytotoxic cell and a specificity for the targeted infected T cells. Such hybrid bi-specific antibodies can include two different Fab moieties, one Fab moiety having antigen specificity for the targeted epitopes, and the other Fab moiety having antigen specificity for a surface antigen of a cytotoxic cell, such as CD3 or CD8. The bi-specific antibodies of the invention can be a single antibody having two specificities, or a heteroaggregate of two or more antibodies or antibody fragments. See, e.g., C. Reading, U.S. Pat. Nos. 4,474,893 and 4,714,681; Segal et al.; U.S. Pat. No. 4,676,980.

While MAbs of the invention can be used for in vivo applications, they may also be used in extra-corporeal ex-vivo applications. The infected T cells in the circulation of the patients can be removed by an affinity matrix (antibody immobilized on a solid phase) which is conjugated with the MAbs of the invention.

Another use for the MAbs of the invention (or for the immunoconjugates of the invention described above) is for determining numbers and relative proportions of infected T cells. The MAbs of the invention can be used in an assay in which infected T cells are bound and their relative numbers are determined. This could be useful in indicating the patient's disease status. For such an assay, the MAbs of the invention can be used in standard assays which are used to determine cell surface antigens. In general, the MAbs are allowed to bind to the infected cells in the leukocyte sample. The detection of the binding can be accomplished by conventional cell staining procedures, for example, a fluorescently labeled second antibody can be used to detect binding of antibody.

The MAbs of the invention can also be used in serotyping of HIV-1 variants either by neutralization assays or binding assays. The manner of performing these assays is well-known by those skilled in the art.

The synthetic or recombinant peptides of the invention and the anti-idiotypic antibodies of the invention can be used in assays to detect the presence of antibodies or MAbs of the invention in a serum sample. These peptides or anti-idiotypes can be used in a standard assay format, well known to those skilled in the art.

The invention will now be further described with reference to specific examples.

GENERATION AND SCREENING OF MABS AGAINST HIV-1 GP120

To generate the G3-136 mAb, affinity purified HIV-1 IIIB gp120 was used to immunize male BALB/c mice. The envelope glycoprotein, gp120, of HTLV-IIIB was prepared from H9/HTLV-IIIB cell extracts. H9/HTLV-IIIB cells were lysed with a lysing buffer consisting of 10 mM Tris-HCl, pH 7.5, 120 mM NaCl, 1 mM $MnCl_2$, 0.5% Triton X-100 and 0.1 mM phenylmethyl sulfonyl fluoride. The extracts were heat-inactivated for 1 hour at 56° C. and reacted with lentil-Sepharose (Sigma, St. Louis, Mo.). The bound fraction was eluted and incubated with Affigel-10 coupled with a murine MAb against gp120 (BAT123). See Fung et al. *Biotechnology*, 5:940–946 (1987). The viral gp120 fraction was eluted and used as the immunogen.

Male BALB/c mice were immunized with 25 μg of protein in Freund's complete adjuvant and three subsequent immunizations of 25 μg in the same adjuvant at 1-month intervals. Three days after the final booster immunization, the mice were sacrificed and spleen cells were isolated and fused with Sp2/0 myeloma cells as described by Fung et al., (supra). Hybrids were selected by supplementing the growth medium with 0.1 mM hypoxanthine, 0.4 μM aminopterin and 16 μM thymidine. Two weeks later, supernatants were collected from the wells of the microtiter plates.

The culture supernatants from the wells of microdilution plates with hybridomas were tested for reactivity with gp120 as coating antigen by enzyme-linked immunosorbent assays (ELISA). Culture supernatants showing strong gp120 reactivity were tested for staining live HIV-1 IIIB-infected cells by an indirect immunofluorescence method. Hybrids from selected fusion wells were expanded and cloned. MAbs from hybridomas selected for further characterization were produced in mouse ascites fluid and purified by protein A affinity chromatography.

Further screening of the hybridomas was then carried out as follows. Wells of Immunlon 2 microdilution plates (Dynatech, Chantilly, Va.) were coated overnight at room temperature with 100 μl of purified gp120 (0.1 μg/ml) in phosphate buffered saline ("PBS"). They were then treated with 5% BLOTTO in PBS for 1 hour at room temperature and washed with PBS containing 0.05% Tween 20 (PBST). Next, 100 μl of test culture supernatant were added to each well for 1 hour at room temperature. The wells were then washed and incubated for 1 hour at room temperature with horseradish peroxidase-conjugated goat anti-mouse IgG (Jackson ImmunoResearch Laboratories, Inc., West Grove, Pa.) diluted in PBST containing 1% BSA (PBSTB). After another washing step, bound antibodies were detected by reaction with 0.1% tetramethyl benzidine and 0.0003% hydrogen peroxide as substrates. The optical density (OD) of the reaction solution was read at 450 nm by an ELISA reader.

Whole HIV-1 virion was used as the immunogen for producing BAT085. The immunization, fusion and screening procedure used in creating BAT085 is essentially the same as described above for G3-136, and is described in detail in published International Application No. PCT/US88/01797.

NEUTRALIZATION ACTIVITY AND SPECIFICITY

Antibodies from reactive wells were then characterized for neutralizing activity by syncytium forming assays. The syncytium-forming microassays using CEM-SS cells were performed as described in detail in Fung M. S. C. et al., *J. Immunol.* 145:2199–2206 (1990). Briefly, 50 µl of diluted MAb were mixed with 50 µl of viral culture supernatant containing 200 syncytium-forming units (SFUs) of HIV-1 IIIB, HIV-1 MN, or HIV-1 RF, and incubated for 1 hour at room temperature. The mixtures were added into microculture wells containing $5 \times 10^4$ DEAE-dextran-treated CEM-SS cells, and the cell cultures were maintained in 5% $CO_2$ at 37° C. for 3 to 4 days. The syncytia were then enumerated under an inverted microscope. The neutralizing activity was expressed as $ID_{50}$, defined as the concentration required to achieve 50% inhibition of the infection (i.e. Vn/Vo=50%), where Vn is the SFUs in the test wells and Vo the SFUs in the control without test antibodies.

BAT085 neutralized IIIB with $ID_{50}$ of 12.5 µg/ml. It did not neutralize MN and RF. G3-136 neutralized IIIB and RF with $ID_{50}$ of 16 and 2 µg/ml, respectively. It did not neutralize MN. Their neutralizing activities against the infectivity of several primary HIV-1 isolates were also tested by using PHA-activated PBMCs by the protocol described in Daar, E. et al., Proc. Nat'l. Acad. Sci. USA 87:6574–6578 (1990). BAT085 neutralized 2 (LS and RP) of 6 isolates tested with $ID_{50}$ of less than 1 µg/ml; G3-136 neutralized 3 (AC, LS and TB) of 7 isolates with $ID_{50}$ ranging from 0.03 µg/ml to 0.4 µg/ml.

SPECIFICITY

In the study of the binding specificity of BAT085 for peptide V15P, which has the sequence of SEQ ID NO:1, the neutralizing activity of BAT085 at 12.5 µg/ml ($ID_{50}$) was tested for inhibition by incubating the antibody with varying concentrations of the peptide for 20 minutes at room temperature, prior to the addition of the viral inoculum of 100 SFUs of HIV-1 IIIB. Irrelevant peptide α-endorphin (Peninsula Laboratories, Belmont, Calif.) was used as control. In this study, the paptide V15P inhibited the neutralizing activity of BAT085. The irrelevant control peptide had no effect.

FLOW CYTOMETRY

The binding of BAT085 and G3-136 to H9 cells infected with HIV-1 IIIB, MN, or RF was analyzed by flow cytometric methods using a Coulter EPIC cell analyzer (Coulter Electronics, Hialeah, Fla.). The bound MAb was detected by fluorescein-conjugated goat anti-mouse IgG (Jackson ImmunoResearch Laboratories, Inc.).

The results show that BAT085 at 10 µg/ml stained 87% and 35% of H9 cells infected with HIV-1 IIIB and HIV-1 MN, respectively. It did not stain H9 cells infected with HIV-1 RF. G3-136 stained 73% and 91% of H9 cells infected with HIV-1 IIIB and HIV-1 RF, respectively, but did not stain H9 cells infected with HIV-1 MN.

EPITOPE MAPPING

Preliminary epitope mapping was performed using nitrocellulose strips impregnated with sequence-overlapping synthetic oligopeptides (9–15 amino acid residues) encompassing the entire length of HIV-1 IIIB gp120 polypeptide chain (from S. Petteway formerly of Du Pont Colo., Wilmington, Del.). The amino acid sequences were derived from HIV-1 HXB2 clone, as described in Myers G., et al. eds., *Human Retroviruses and AIDS*. Los Alamos National Laboratories, Los Alamos, N. Mex. (1989). Amino acid sequences of the synthetic peptides for the other HIV-1 isolates, MN and RF, were also obtained from Myers et al., supra.

The reactivity of anti-HIV-1 gp120 MAbs with these peptides was determined by the methods described in Liou R. S. et al., *J. Immunol.* 143:3967–3975 (1989). Briefly, the nitrocellulose strips were incubated overnight at room temperature with test MAbs at 10 µg/ml in 5% BLOTTO. The strips were then washed with PBST. The bound antibody was then detected by incubating the strips with diluted horseradish peroxidase-conjugated goat anti-mouse IgG (Jackson ImmunoResearch Laboratories, Inc.) for 1 hour at room temperature. The strips were washed and the color reaction developed with a substrate solution containing 0.3% 4-chloro-1-naphthol and 0.005% hydrogen peroxide.

Further fine epitope mapping was performed by peptide ELISA. Wells of Immulon 2 microtest plates were coated overnight at room temperature with 100 µl of the synthetic peptides (1 µg/ml) in PBS. The wells were then treated with 5% BLOTTO for 1 hour at room temperature. After the wells were washed with PBST, 100 µl of BAT085 or G3-136 (1 µg/ml) were added to the wells for reaction for 1 hour at room temperature. The wells were then washed and the bound MAb was then detected by horseradish peroxidase-conjugated goat anti-mouse IgG. The color reaction was developed by incubation with the peroxidase substrate solution. Reactivity was regarded as positive if the OD was two-fold higher than that if the wells coated with the irrelevant peptide α-endorphin.

It was found that BAT085 and G3-136 reacted specifically with a peptidic segment having SEQ ID NO:1 (referred to as V15P) in the V2 region of gp120, amino acid residues #169–183. In order to confirm this observation, overlapping oligopeptides encompassing the peptidic segment (amino acid residues: 159–198) in HIV-1 IIIB gp120 (FIG. 1) were synthesized for ELISA and liquid-phase competition assays. When these peptides were used as the solid-phase antigens at 1 µg/ml, BAT085 reacted strongly with the peptide having SEQ ID NO:1 V15P (OD=1.4), and weakly with the peptide having SEQ ID NO:2 L20T (OD=0.13). It did not react with the peptides having SEQ ID NO:3

F15Y, SEQ ID NO:4 V10K, and SEQ ID NO:5 A10P, giving OD less than two-fold of the negative control α-endorphin (OD=0.01). G3-136 also reacted with the peptide having SEQ ID NO:1 V15P (OD=0.44), but did not react with the peptides having SEQ ID NO:2 F15Y, SEQ ID NO:3 L20T, SEQ ID NO:4 V10K, and SEQ ID NO:5 A10P. In the determination of reactivity with different HIV-1 isolates, BAT085 did not react with peptide having SEQ ID NO:6 M15S and SEQ ID NO:7T15P, which correspond to the same region of peptide SEQ ID NO:1 V15P in the gp120 of HIV-1 MN and RF, respectively. G3-136 reacted with the peptide of SEQ ID NO:7 T15P (OD=0.23), but not with the peptide of SEQ ID NO: 6 M15S.

In the liquid-phase competition binding assay examining the effects of peptides on the binding of biotinylated BAT085 to captured gp120, SEQ ID NO: 1 V15P inhibited the binding of BAT085 to gp120 in a dose-dependent manner (FIG. 5). The peptide α-endorphin had no effect even at the concentration of 40 μg/ml.

COMPETITION ELISA

The effects of anti-HIV-1 gp120 MAbs, peptide SEQ ID NO: 1 (amino acid residues: 169–183), and recombinant soluble CD4 (sCD4) on the binding of BAT085 and G3-136 to HIV-1 IIIB gp120 were also determined. The murine HIV-neutralizing MAb BAT123 (IgG$_{l,k}$) binds to the PND in the V3 region of IIIB gp120 (amino acid residues: 308–322). International Application No. PCT/US88/01797. Murine MAb G3-519 (IgG$_{l,k}$) recognizes a component of the CD4-binding domain in the C4 region of gp120 (amino acid residues: 423–437). PCT/US90/02261. Murine MAb G3-4 (IgG$_{2a,k}$) recognizes a conformational neutralizing epitope on HIV-1 gp120. I5e (IgG$_{l,k}$) is an HIV-1 neutralizing human MAb (from J. Robinson, Louisiana State University School of Medicine, New Orleans, La.), which also recognizes a distinct conformational epitope on gp120. The murine MABs were produced from ascites of BALB/c mice (Harlan Sprague Dawley, Inc. Houston, Tex.) injected with the hybridomas, and affinity-purified by recombinant protein A-Sepharose (Repligen, Boston, Mass.). I5e was produced from culture supernatant of the hybridoma and purified by protein A affinity chromatography. Polyclonal anti-HIV-1 gp120 antibodies (D6205) (International Enzymes, Inc., Fallbrook, Calif.) were generated by immunizing sheep with a synthetic peptide encompassing a highly conserved peptidic segment in the carboxy terminus of HIV-1 (BH-10 strain) gp120 (amino acid residues: 497–511). The antibodies were isolated from the sheep hyperimmune sera by affinity chromatography using the specified synthetic peptide coupled to Sepharose.

Wells of Immunlon 2 microtest plates were coated overnight at room temperature with 50 μl of 5 μg/ml of affinity purified sheep anti-HIV-1 gp120 (D6205, International Enzymes, Inc.). The wells were then treated with 5% BLOTTO for 1 hour at room temperature. Fifty μl of purified gp120 (0.5 μg/ml) was then added to each well for incubation for 2 hours at room temperature. The plates were then washed. One hundred μl of diluted biotinylated MAb was added to the wells with or without varying amounts of competing MAbs (including BAT085, G3-136, G3-4, BAT123, G3-519, and I5e), peptide SEQ ID NO:1 V15P or sCD4. The biotinylated MAbs were used at dilutions which gave half-maximal binding to the captured gp120. The incubation time was 1 hour at room temperature. The plates were washed, and reacted with 100 μl of horseradish peroxidase-conjugated streptavidin (diluted 1:2,000 in PBSTB) (Jackson ImmunoResearch Laboratories, Inc.) for 1 hour at room temperature. The plates were again washed and allowed to react with the peroxidase substrate solution as described above. The degree of inhibition was expressed as the percent decrease in OD in the test wells when compared with the control wells without the inhibitors.

The binding of biotinylated BAT085 to gp120 was partially inhibited by G3-4 (80%) and G3-136 (65%) at 40 μg/ml. By contrast, BAT123, G3-519, and I5e had no effect. Unconjugated BAT085 at 40 μg/ml abolished completely the binding. When the binding of biotinylated G3-136 to gp120 was tested, G3-4 inhibited the binding as effectively as G3-136. However, BAT085 inhibited the binding by only 33% even at 40 μg/ml, and BAT123, G3-519, and I5e had no effect.

To examine whether the neutralizing epitope mapped to the V2 region was involved in the interaction between CD4 and gp120, the effect of sCD4 on the binding of the biotinylated MAbs to captured gp120 was tested. sCD4 inhibited the binding of G3-136, G3-4 and G3-519 to gp120, although not completely even at a concentration as high as 40 μg/ml. The binding of BAT85 and BAT123 to gp120 is not affected by sCD4. These results suggest that the epitopes recognized by BAT085 and G3-136 may be different.

RIPA

A radioimmunoprecipitation (RIPA) procedure was carried out to determine the effect of reducing the disulfide linkages and deglycosylsation on binding. Briefly, HIV-1 IIIB-infected H9 cells were metabolically labeled for 4 hours with [$^{35}$S] cysteine and [$^{35}$S] methionine (100 μCi/ml; ICN Pharmaceuticals, Inc., Irvine, Calif.) and suspended in a RIPA lysing buffer (50 mM Tris hydrochloride [pH 8.0], 150 mM NaCl, 1% Triton X-100, 1% sodium deoxycholate, 0.1% sodium dodecyl sulfate, 1 mM phenylmethylsulfonyl fluoride). To examine the effect of antibody binding to gp160/gp120 after reduction of disulfide linkages, the metabolically labeled cell lysates was treated with 0.1M dithiothreitol in PBS at 37° C. for 1 hour. Dithiothreitol was then removed by dialysis. The effect of deglycosylation of gp160/gp120 on the antibody binding was also examined by treating the cell lysates with 100 mU/ml Endo H for 2.5 hours at 37° C. The treated or untreated lysates were precleared with protein A-Sepharose bound to rabbit antiserum to mouse kappa light chain (κ-PAS) for 3 hours at room temperature. RIPA was performed by adding 3 μg of purified MAb (BAT085, G3-136 or G3-4) and 0.2 ml of a 10% suspension of κ-PAS to 200 μl of labeled and clarified lysate. The samples were incubated for 18 hours at 4° C., and the beads were washed with the RIPA lysing buffer. The pellets were suspended in electrophoresis sample buffer and boiled for 3 minutes. Proteins were analyzed by sodium dodecyl sulfate-polyacrylamide gel electrophoresis, followed by autoradiography.

As summarized in FIG. 1, the reactivity of G3-136 with gp120 in a RIPA was reduced when the viral lysate was first denatured by dithiothreitol. When a radio-labeled HIV-1 lysate was subjected to Endo H digestion, the partially deglycosylated product of 90–100 kD was weakly recognized by G3-136. In parallel experiments, the reactivity of BAT085 with reduced or deglycosylated gp120 was unaltered, whereas the reactivity of G3-4 with gp120 was completely abolished under these conditions.

The foregoing terms and expressions are descriptive only and not limiting, and the invention is defined in the claims which follow, and includes all equivalents of the subject matter of the claims.

What is claimed is:

1. A monoclonal antibody which is produced by the hybridoma cell line deposited at the ATCC, Rockville, Md. under Accession number HB 10932.

2. The monoclonal antibody of claim 1 which is a chimeric antibody with variable regions of rodent origin and constant regions of human origin.

3. The hybridoma deposited at the ATCC, Rockville, Md., under Accession number HB 10932.

4. The monoclonal antibody of claim 1 wherein the antigen binding sites are of rodent origin, and the remainder of the antibody is of human origin.

* * * * *